United States Patent [19]

Mannfeld

[11] 4,308,106
[45] Dec. 29, 1981

[54] PROCESS FOR REMOVING SUBSTANTIALLY ALL WATER FROM AN ALCOHOL-CONTAINING SOLUTION FOR USE AS A MOTOR FUEL OR MOTOR FUEL ADDITIVE

[76] Inventor: Robert L. Mannfeld, 5549 Surrey Hill Ct., Indianapolis, Ind. 46226

[21] Appl. No.: 174,714

[22] Filed: Aug. 1, 1980

[51] Int. Cl.³ .............................................. B01D 3/10
[52] U.S. Cl. ........................................ 203/19; 203/24; 203/26
[58] Field of Search ............................ 203/19, 24, 26; 202/173

[56] References Cited

U.S. PATENT DOCUMENTS 1,860,554  5/1932  Ricard et al. ......................... 203/19
3,486,985  12/1969  McGrath ............................. 202/173

Primary Examiner—Frank Sever
Attorney, Agent, or Firm—Woodard, Weikart, Emhardt & Naughton

[57] ABSTRACT

A process and still for removing substantially all water from an alcohol-containing solution. The solution is distilled in a rectification column under reduced pressure of about 40 mm Hg or less, and the distillate later collected and condensed having a water content of about 2% by volume or less. Heating for distilling the original solution and cooling for condensing the distilled alcohol vapors are supplied to the system by an external, closed-loop heat pump.

6 Claims, 1 Drawing Figure

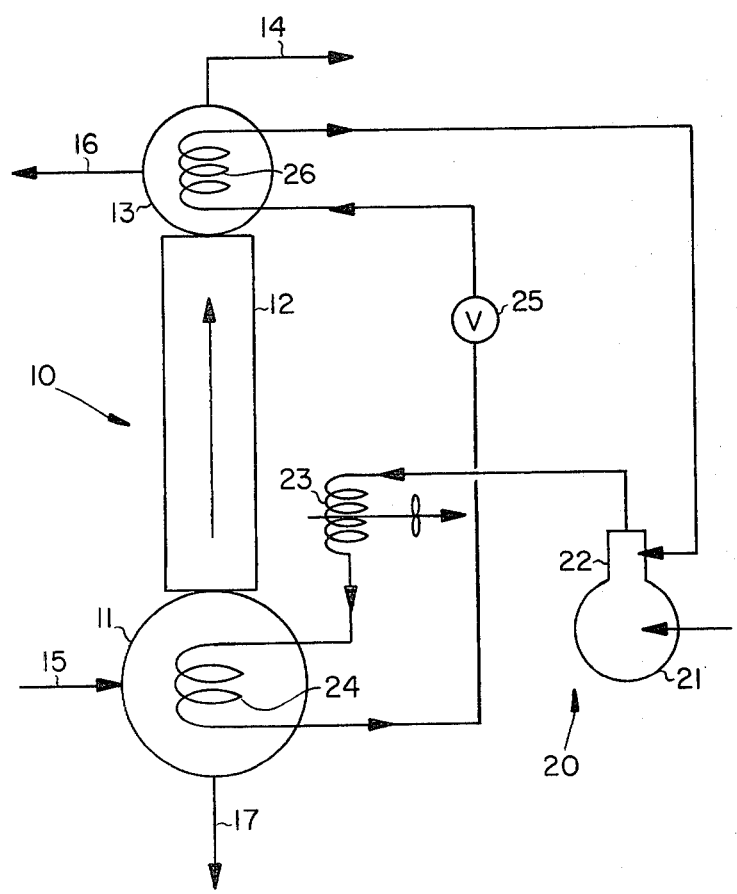

PROCESS FOR REMOVING SUBSTANTIALLY ALL WATER FROM AN ALCOHOL-CONTAINING SOLUTION FOR USE AS A MOTOR FUEL OR MOTOR FUEL ADDITIVE

BACKGROUND OF THE INVENTION

This invention relates generally to alcohol distillation and, in particular, to the removal of substantially all water from an alcohol-containing solution leaving substantially anhydrous alcohol suitable for gasohol and other industrial applications.

Alcohols, generically, are compounds having the formula ROH, in which R is any alkyl or substituted alkyl group. Alcohols may be primary, secondary or tertiary. They may be straight chains or cyclic.

Ethyl alcohol, ordinarily termed "alcohol," is one of the simplest of these alcohols . . . and one of the most important. Its uses are so many and varied that it literally can be said to be indispensable in our lives. Industrial applications include use as solvents for lacquers, varnishes, perfumes and flavorings and use as media for chemical reactions and recrystalizations. More direct uses are in "alcoholic" beverages, in the medical field and as fuels for lamps, burners and the like. One burgeoning use of great magnitude is for mixing with gasoline to produce gasohol for fueling internal combustion engines such as those powering automobiles, trucks and tractors.

Industrial production of ethyl alcohol is generally by one of three processes . . . esterification-hydrolysis, direct hydration, or fermentation of carbohydrates. Of these, fermentation is by far the greatest commercial producer and the only method used for on-the-farm production of ethyl alcohol for gasohol or motor fuel. It involves the decomposition, i.e., fermentation, of sugars in the presence of yeasts into alcohol and carbon dioxide. Commercial sources for these sugars are molasses obtained from sugarcane and starches found in potatoes and various grains such as corn, rye, rice and barley. The solution obtained from the fermentation process is commonly called "beer," in which ethyl alcohol is present as about an 8–10% solution. This highly aqueous beer solution is not usable as a motor fuel or motor fuel additive. Nearly all of the water fraction must first be removed.

To refine the beer solution into usable alcohol, the mixture is purified by fractional distillation.

Distillation, in general, involves producing a gas or vapor from a liquid by heating the same in a vessel and then collecting and condensing the vapors back into liquid form. Fractional distillation adds the feature of returning a portion of the condensate to a column on top of a still to effect a reflux and countercurrent contact with the rising vapor. Various impurities may also be removed during this fractional distillation process. Some of these may be aldehydes, ketones and other low-boiling impurities and fusel oils and other high-boiling constituents. The usual end product of this distillation at atmospheric pressure is a mixture of 95% alcohol and 5% water, known simply as 95% alcohol. It has many uses including being usable directly as a motor fuel in certain vehicles, particularly those used in modern farming operations. However, it is not acceptable as a motor fuel additive, as it still contains too much water and will separate from gasoline at usual ambient temperatures.

To avoid this problem, there is a need for "absolute alcohol," meaning a substantially anhydrous ethyl alcohol having no more than trace amounts of water in solution. Demand for this material has greatly increased in recent years along with anxieties over decreasing petroleum supplies and the skyrocketing price of gasoline in this country. Gasohol, a generic name for a mixture of gasoline and absolute alcohol, currently preferred in a 90% to 10% proportion by volume, has received much publicity as the panacea in future years as oil supplies dwindle ever more rapidly. The 95% alcohol product alone is not practicable for this use because it requires a third component such as benzene or ether to permit a stable mix with gasoline for use in internal combustion engines. Absolute alcohol requires no such additional blending agent, as it is miscible with gasoline in all proportions.

With the ready availability of 95% alcohol through distillation, it might be expected that obtaining 100% (water free) alcohol would provide little problem. This is not the case. For no matter how efficient or long the distillation process, 95% alcohol or any lower-strength solution cannot be further concentrated beyond about a 96.4% alcohol solution by weight under standard conditions. At approximately that point, an equilibrium is reached in which the liquid and vapor mixtures have the same composition. This is called an azeotrope or a constant-boiling mixture. In the case of ethyl alcohol, this is a binary azeotrope of the minimum-boiling variety. It has been reported that pressure changes affect this azeotropic mixture. Theoretically, complete separation of ethanol and water has been reported to be possible at 70 mm Hg and about 28° C. That same report [(*J. PERRY, CHEMICAL ENGINEERS' HANDBOOK*, 631 (3rd Ed. 1950)] conditions its conclusion on the assumption that "the [tabulated] data are correct," and further states that complete separation on a commercial scale has been found "difficult to achieve." Applicant is also aware of no such successful application of this principle prior to his present invention.

To satisfy the ever-growing demand for absolute alcohol on a commercial scale, several continuous methods have been used. The first, based on a patent issued to Donald B. Keyes, U.S. Pat. No. 1,830,469, relies upon the dehydration of ethyl alcohol by the formation of a ternary azeotrope with benzene, ethyl alcohol and the remaining water in a 95% alcohol solution. This azeotropic mixture, having a low boiling point, is distilled off and must be separated by further secondary operations, leaving anhydrous ethyl alcohol at the bottom of the rectification column. Many other compounds have been suggested for use in similar azeotropic distillations, including ethyl ether, methylene chloride, isobutylene, isooctane, gasoline, benzene and naptha, isopropyl ether, methyl alcohol and acetone. All of these distillations suffer from similar problems, however, those being increased cost and increased danger from fire or explosion during processing due to the added components.

A second process, based on a patent to Joseph Van Ruymbeke, U.S. Pat. No. 1,459,699, relies upon a reflux of glycerine in the column to act as a dehydrating agent. The glycerine and water purportedly pass out at the bottom of the still with the distillate being anhydrous ethyl alcohol. Considerable alcohol is caught up with the glycerine and water, however, and must be recovered in a second rectifying still.

Yet another method, reported to be the earliest of its kind, utilizes anhydrous potassium carbonate as the drying agent. Many other inorganic compounds have been similarly studied, such as calcium oxide, calcium carbide, calcium sulfate, calcium aluminum oxide, aluminum and mercuric chloride, zinc chloride and sodium hydroxide, some of which are suggested as additives in the glycerine refluxing process mentioned above.

The immediate need for a practicable method for making substantially anhydrous alcohol is possibly greatest with the private farmer. He is experiencing ever-increasing costs, not the least of which is the cost of gasoline and diesel fuel to operate his farm machinery. At the same time, he has an available supply (and often surplus) of grains which can readily be fermented to produce a beer solution low in alcohol content. He needs to be able to concentrate that solution into a usable motor fuel and motor fuel additive. In all of the above processes, a farmer must use chemical processing equipment not usually found on a farm. For example, in distillation of alcohol he would normally use an open-fired still or a boiler for steam generation and would use well water for cooling. The use of such equipment for the processing of flammable solvents such as ethyl alcohol, particularly in concentrated form, is not a safe operation under usual farm conditions.

The end result of all of this is that no safe practicable process for making substantially anhydrous alcohol has yet been discovered which is suitable for operation by the average farmer or other person relatively unskilled in chemical technology. The known processes are complex, require other additives (such as benzene or ether) which significantly increase cost and potential hazard during use, and fail to provide a safe, efficient, simple method of operation. The applicant's invention described and claimed hereinbelow attempts to meet this need.

SUMMARY OF THE INVENTION

The applicant's invention is a unique combination of two technologies, comprising a process for removing substantially all water from an alcohol-containing solution. It first makes use of a distillation process with reflux in which the column is placed at reduced pressure of about 40 mm Hg or less and is maintained at such a pressure during the distilling operation. The recovered distillate is substantially anhydrous, having a water content of about 2% or less, and is usable directly as a motor fuel or as an additive with gasoline for making gasohol that will not phase separate at normal operating temperatures. It second makes use of an external, closed-cycle heat pump to provide safe, economical heat for distillation and at the same time to provide a cooling medium for condensing the alcohol product. This is a refrigeration cycle in which, due to the column being operated at reduced pressure, the temperature for condensing the refrigerant gas is appropriately matched to the boiling temperature of the alcohol solution and the evaporating temperature of the refrigerant is also appropriately matched to the condensation temperature of the substantially anhydrous alcohol being produced.

In one mode of practicing the above process, substantially anhydrous ethyl alcohol can be recovered from an initial beer solution, an initial 95% alcohol solution, or any concentration inbetween. The recovered alcohol is suitable for a great many commercial uses, not the least of which is in gasohol production for internal combustion engines.

Related objects of the present invention will become evident from the following description.

BRIEF DESCRIPTION OF THE DRAWINGS

FIG. 1 is a schematic diagram illustrating the preferred distillation process and still of applicant's present invention.

DESCRIPTION OF THE PREFERRED EMBODIMENT

As previously explained, applicant's invention combines the use of a refrigeration cycle (heat pump) as a means for providing the heating and cooling needs for a distillation, or rectification, column that operates at reduced pressure in order to remove substantially all water from an alcohol-containing solution. The recovered distillate contains substantially anhydrous alcohol usable in ever-growing commercial applications. Applicant's process accomplishes this without the need for addition of benzene or any other dehydrater or entrainer compound.

In so doing, applicant makes use of the fact that a change in the boiling point of a positive azeotropic mixture results in a corresponding change in the composition itself. In the case in point, reducing pressure in the rectification column reduces the boiling point of the solution and increases the vapor composition of ethyl alcohol as the component having the lesser molecular latent heat of vaporization. The binary azeotrope of alcohol and water is reported, in the reference previously mentioned, to change from approximately 96.6% alcohol by weight at atmospheric pressure to nearly 100% alcohol by weight at absolute pressures below approximately 70 mm Hg. Applicant's experiments to date with his preferred process and still have shown that a pressure of about 40 mm Hg or less is preferred for an efficient and practicable recovery. Applicant also makes use of the fact that distillation at reduced pressures changes the shape of the equilibrium curve for alcohol and water in a way that reduces the number of theoretical plates necessary to bring about complete separation.

Applicant has coupled this technology with the advantages of a heat pump, which for the still used in applicant's preferred process provides heat at moderate temperatures to boil the alcohol and then removes that heat at lower temperatures to condense the alcohol vapors following distillation. The still operates at low absolute pressure (down to about 20 mm Hg and less) and provides a motive force that is both practicable and energy efficient. Moreover, applicant has found that the temperatures required to condense and evaporate normal refrigerants used in such heat pumps are uniquely and appropriately matched to the boiling and condensing temperatures, respectively, for ethyl alcohol at the reduced pressures used in his preferred process and still. In this way, applicant's preferred process permits separation of substantially all water from an alcohol-containing solution without the use of hazardous entrainers or high pressure equipment.

Referring now to FIG. 1, therein is depicted the preferred process and still 10 of applicant's present invention. Still 10 includes a process, or alcohol, boiler 11 integrated with a rectification column 12 and process condenser 13. Column 12 includes a number of plates (not shown) and packing material or the like (not shown), which are standard for such columns to achieve vacuum separation and fractionation of solution components. A vacuum source (not shown) such as a standard vacuum pump is provided initially to place the boiler, column and condenser under reduced pressure through line or pipe 14 and then to maintain the same throughout the distillation operation. The solution to be separated is fed batchwise into the still through pipe 15. The substantially anhydrous distillate product is withdrawn from condenser 13 through pipe 16 while the bottom product, commonly called "slop" (mostly waste water), is drawn off boiler 11 through pipe 17.

Applicant's preferred energy source is an external, closed-loop heat pump 20. It includes a standard air conditioning compressor 21 placed in series through piping with an oil separator 22, a desuperheater 23, an alcohol boiler-refrigerant condenser 24, an expansion valve 25 and an alcohol condenser-refrigerant evaporator 26.

The overall operation of applicant's preferred still 10 is as follows:

Boiler 11 is first charged through pipe 15 with an initial alcohol- and water-containing solution to be separated. This solution may range from beer with only about 8–10% alcohol to industrial grade 95% alcohol. One specific goal of applicant's process in this regard is to provide a farm still that will produce nearly anhydrous alcohol (199 proof) from the usual distilled strength of farm-produced alcohol which has between about 50% and 95% initial alcohol concentration. Boiler 11, column 12 and condenser 13 are then placed at reduced pressure by operation of a vacuum source (not shown) through pipe 14. This reduced pressure can vary, per relationships described hereinbelow, but applicant has found pressures of about 40 mm Hg or less are required to remove substantially all water from the recovered alcohol product. In this regard, "removal of substantially all water" as used herein is meant to define the removal of about 98% or more of the water from an initial alcohol-containing solution, leaving a distillate product having a water content about 2% or less. "Substantially anhydrous alcohol" as used herein is meant to define the same limitation and distillate product, with all percents (%) being given as percent by volume of a given liquid or solution.

In the separate closed-loop heat pump 20, a refrigeration medium such as Freon-12 is compressed to a superatmospheric pressure in the range of about 150 psig from about 30 psig by means of compressor 21. Considerable heat is thereby generated and the hot gasses from the compressor are passed through oil separator 22 (to return excess oil to the compressor) to desuperheater 23. At that point, the hot gasses are partially cooled so that only sufficient heat to boil and condense the alcohol is recirculated in the system. Too much heat removed at this point would cool the total system, while too little heat removed would cause it to overheat. The operation of such desuperheaters is common in the art and not unusual to applicant's present invention.

The desuperheated gasses are then directed to refrigerant condenser 24 and alcohol reboiler 11. At that point, the gasses give up their heat to boil the solution at reduced pressure. The alcohol vapors thereby generated pass up through rectification column 12 to process condenser 13. Meanwhile, the condensed refrigerant leaving evaporator 24 passes through expansion valve 25 for the purpose of substantially reducing its pressure and thereby causing the refrigerant to expand and evaporate and thus effect a reduction in temperature.

At the top of the column, the alcohol vapors are collected and condensed in condenser 13 by contact with refrigerant evaporator 26. The evaporator is cooled by the same refrigerant that first gave up heat to boil the alcohol originally and then further expanded and cooled as it passed through expansion valve 25. Now, as the alcohol vapors condense, heat is transferred back to the refrigerant which leaves the evaporator in an expanded, heated state as it finishes the cycle returning to compressor 21. In this way, the same heat in the original hot refrigerant gasses passes to the alcohol, up the column, and then back to the refrigerant which returns to the compressor for further compression thereby completing the cycle that is common to an external, closed-loop heat pump of this type.

Meanwhile, at the top of the column not all of the recaptured alcohol is removed from the still during operation. A major portion of the product stream is returned to the process as a liquid reflux of alcohol dripping down through the rectification column countercurrent to the rising alcohol vapors. Under proper conditions, which are known to those of ordinary skill in this art, this countercurrent reflux contact results in enrichment of the rising vapor stream in the lower boiling component (in this case alcohol) and enrichment of the falling liquid stream in the higher boiling component (in this case water). The amount of recaptured condensate permitted to reflux and the "reflux ratio" (being the quantity of liquid reflux per unit quantity of product removed from the processed unit) help to determine the water content in the final condensed distillate and the ultimate success of the process.

Generally, applicant has found that the degree of vacuum, or the absolute pressure, in the column ultimately determines the end concentration of the distillate. This pressure is directly related to the required reflux ratio and the boiling point of the solution, and is also directly related to the number of plates and column height needed to achieve a given product concentration. It can also be stated that with lower alcohol concentration in the initial solution to be separated, column height must be increased possibly with additional plates or decreased pressure to compensate for the greater concentration difference between the original and end solutions. The precise parameters used, just as the other dimensional considerations for the still, are easily and simply determined by experimental procedures common to the art and are not essential or critical to the advantages provided by applicant's process. Moreover, applicant's preferred process as described herein is a batch process. It is clear that a continuous-feed process can be simply and easily substituted and is within the scope and contemplation of applicant's invention.

There may also exist other components or impurities present in the original solution to be separated by applicant's process. These components such as light fraction aldehydes and ketones or heavy fraction fusel oils may vary somewhat the product stream removed from the condenser, but they do not detract from the unprecedented water-removal capability of applicant's process and still. These other components can be removed by secondary operations before or after distillation, if desired, or may be left in the product during its subsequent commercial use.

To better understand the preferred process and still of applicant's present invention, the following specific examples are provided.

EXAMPLE 1

A portable, skid-mounted still was constructed incorporating applicant's preferred process and still as illustrated in FIG. 1. To the process boiler was first added a 10 gallon solution of 95% alcohol. The boiler, the condenser and the 10 foot packed rectification column therebetween was then placed at a reduced pressure of 20 mm Hg. An external, closed-loop heat pump was then activated using Freon-12 as the refrigerant. The Freon-12 gas was compressed to a pressure of 150 psig and was delivered through a desuperheater to a refrigerant condenser-alcohol boiler at approximately 35° C. Heat was thereby transferred to the solution which boiled at a temperature of 24° C. The distilled vapors passed up through the column as the condensed refrigerant was further cooled upon expansion to a temperature of about −7° C. The alcohol vapors were collected and condensed, through indirect contact with the refrigerant in a refrigerant evaporator-alcohol condenser, at a temperature of 4° C. and a reflux ratio of 14:1. After reaching equilibrium in about one hour, the withdrawn portion of the product was tested and found to contain 99% ethyl alcohol and 1% water. At this concentration, the substantially anhydrous alcohol product was mixed with gasoline to make gasohol and used successfully as a motor fuel for an internal combustion engine.

EXAMPLE 2

The process and still in Example 1 was used except that a reduced pressure of 25 mm Hg was maintained in the distillation column. The original solution boiled at 27° C. and the alcohol vapors condensed at 14° C. Equilibrium was reached and after thirty minutes of operation using a reflux ratio of 14:1, product was drawn off and analyzed to contain 98.5% alcohol and only 1.5% residual water.

EXAMPLE 3

The process and still in Example 1 was used except that an original solution containing 30% alcohol was distilled. The column was maintained at 40 mm Hg and the solution boiled at 35.5° C. and the alcohol vapors were condensed at 20° C. Equilibrium was reached and after 30 minutes of operation using a reflux ratio of 14:1, condensate product was drained off and analyzed to contain 98% alcohol and only 2% water.

EXAMPLE 4

The process and still in Example 1 were used except that a 15-foot packed rectification column was substituted and a 7% alcohol solution was distilled. The column was maintained at 18 mm Hg, and the solution boiled at 38° C. The alcohol vapors were condensed at 4.5° C. Equilibrium was reached after 1 hour of operation using a reflux ratio of 14:1. The condensate was drained off and analyzed to contain 98% alcohol and only 2% water.

I claim:

1. A process for removing substantially all water from an ethyl alcohol-containing solution, comprising the steps of:
   (a) charging a boiler with an ethyl alcohol- and water-containing solution;
   (b) distilling the solution in the absence of an entrainer in a single distillation column with reflux to achieve a distillate having a water content of about 2% or less by volume;
   (c) placing the column under reduced pressure of about 40 mm Hg or less and maintaining the same during said distilling;
   (d) collecting and condensing the distillate in a condenser; and
   (e) supply heating for said distilling and cooling for said condensing from a heat pump.

2. The process in claim 1 additionally comprising using the distillate as a motor fuel either as produced or in combination with other ingredients.

3. The process in claim 1 wherein said charging is with a solution containing at least about 50% ethyl alcohol.

4. The process in claim 1 wherein said charging is with a solution containing at least about 95% ethyl alcohol.

5. The process in claim 1 in which said charging is with a beer solution.

6. The process in claim 1 in which the distillate has a water content of about 0.5% or less.

* * * * *